United States Patent [19]

Helsley et al.

[11] 4,327,103

[45] Apr. 27, 1982

[54] 3-{3-[4-(4-FLUOROBENZOYL)PIPERIDYL]-PROPYL}-2-METHYL INDOLE

[75] Inventors: Grover C. Helsley, Pottersville; Joseph T. Strupczewski, Flemington, both of N.J.; Beth A. Gardner, San Jose, Calif.

[73] Assignee: Hoechst-Roussel Pharmaceuticals Incorporated, Somerville, N.J.

[21] Appl. No.: 166,419

[22] Filed: Jul. 7, 1980

[51] Int. Cl.³ .................. A61K 31/445; C07D 403/06; C07D 401/06
[52] U.S. Cl. ..................................... 424/267; 546/201
[58] Field of Search ........................ 546/201; 424/267

[56] References Cited

U.S. PATENT DOCUMENTS 3,980,658 9/1976 Possanza et al. .................... 546/201
4,046,900 9/1977 Helsley et al. ...................... 546/201

*Primary Examiner*—John M. Ford
*Assistant Examiner*—N. Harkaway
*Attorney, Agent, or Firm*—Jerome Rosenstock

[57] ABSTRACT

A neuroleptic agent is disclosed. The agent is 3-{3-[4-(4-fluorobenzoyl)piperidyl]propyl}-2-methylindole or an acid addition salt thereof prepared from a pharmaceutically acceptable acid.

4 Claims, No Drawings

3-{3-[4-(4-FLUOROBENZOYL)PIPERIDYL]-PROPYL}-2-METHYL INDOLE

DESCRIPTION OF THE INVENTION

This invention relates to a neuroleptic agent and more particularly to 3-{3-[4-(4-fluorobenzoyl)-piperidyl]}-2-methyl indole or an acid addition salt thereof prepared from a pharmaceutically acceptable acid.

To the best of our knowledge, the compounds of the present invention have not heretofore been described. U.S. Pat. No. 4,046,900 describes benzoylpiperidyl alkylindoles generally and in particular 3-{3-[4-(4-fluorobenzoyl)piperidyl]propyl}indole which exhibit tranquilizing properties. Surprisingly and unexpectedly, the compounds of the present invention exhibit neuroleptic or tranquilizing properties without exhibiting the degree of or propensity towards production of extrapyramidal side effects such as are exhibited by the prior art neuroleptic agents heretofore described.

Such extrapyramidal side effects, such as parkisonism-like syndrome, dyskinetic-dysotonic reactions and akathesia, are common to most neuroleptics and are expected. The lack or small degree thereof exhibited by the subject compounds is unexpected and surprising.

A compound of the invention 3-{3-[4-(4-fluorobenzoyl)piperidyl]propyl}-2-methylindole conforms to the formula

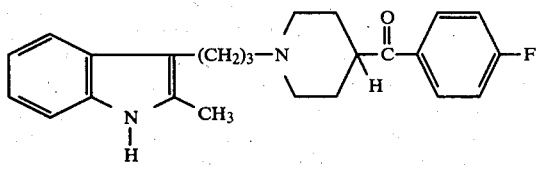

The acid addition salts thereof are prepared from pharmaceutically acceptable acids. Acids useful for preparing the acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The above-described compounds of the invention are generally prepared in the manner described in U.S. Pat. No. 4,046,900, incorporated by reference hereinto.

The compounds of the invention are useful as neuroleptic agents. This activity is demonstrated in a number of standard assays for neuroleptic activity, including prevention of amphetamine toxicity in aggregated mice (AAT).

It is well documented that the aggregation of mice in small chambers greatly increases the toxicity (lethality) of amphetamine. The prevention of this amphetamine lethality by neuroleptic agents has also been verified by many investigators and is generally cited as another indication of neuroleptic activity.

The increased toxicity has been attributed to increased circulating catecholamines and increased behavioral activation induced by aggregation. However, non-neuroleptic sympatholytics and psychosedative agents like the barbiturates are not found to produce reliable dose-related protection. In addition, anxiolytic agents (minor tranquilizers) are also found to be ineffective in prevention of toxicity. The actual mechanism of aggregation enhanced amphetamine toxicity (AAT) is not fully understood, but the selective protection provided does indicate neuroleptic agents and their separation from psychosedative and anxiolytic agents.

The procedure is as follows:

(a) The experimental subjects are randomly selected adult male mice (Chalres River Farms CD-1), 18 to 28 grams and 10 subjects are used at each dose.

(b) The experimental compounds are dissolved or suspended in 10 ml of distilled $H_2O$ plus one drop of "Tween 80" and administered orally with an 18 ga. dosing needle. The "control" subjects receive the $H_2O$-Tween 80 solution and all administrations are in volume proportionate to 1 ml/100 gms. of body weight.

After compound and control dosing the individual treatment groups (N=10) are placed in separate "shoebox" plastic carriers (10.5"L×8"W×6"H) to maintain group integrity prior to d-amphetamine administration.

(c) Sixty minutes after experimental compound administration the mice are dosed with d-amphetamine sulfate by subcutaneous injection (21 mg/kg). The d-amphetamine sulfate is dissolved in distilled water at a concentration of 2.1 mg/cc and immediately after dosing, the mice of each treatment group are aggregated in "stick-cages" in groups of five (e.g. two groups of five for each treatment group).

The "stick-cages" are 10 consecutive cages 10 cm×10 cm×10 cm wire mesh with ¼" holes. These cages are subsequently place in close-fitting, plastic-lined containers consisting of only the floor and 10 cm walls. This aids in the maintenance of elevated temperatures (80°–84° F.) which has been found to be an important parameter. The room temperature should be from 70° to 72° F. during the test but the chamber temperature is constantly monitored so that it does not exceed 85° F., for at extreme temperatures (87°–90° F.) even known neuroleptic agents may not prevent amphetamine induced lethality.

(d) At the end of the first hour post-amphetamine, the unprotected mice begin to expire and to maintain a semblance of the aggregated condition the expired mice are removed and replaced by marked, untreated "scrub" mice. This is done at 15-minute intervals for the following 4 hours which are also convenient intervals for examination of chamber temperatures.

(e) At the end of 5 hours post-amphetamine, the number dead in each treatment group are counted. All control subjects (solvent+amphetamine) should have expired. If fewer than 8 of 10 controls expire during the test it is repeated.

The estimation of the $ED_{50}$ values and 95% confidence limits for protection in this test are calculated by a Probit analysis of the data using the number dosed versus the number surviving.

It has been found that 3-{3-[4-(4-fluorobenzoyl)-piperidyl]propyl}indole, revealed in U.S. Pat. No. 4,046,900 has an $ED_{50}$ of 4.6 mg/kg orally while the compound of the invention, 3-{3-[4-(4-fluorobenzoyl)-piperidyl]propyl}-2-methyl indole has an $ED_{50}$ of 6.1 mg/kg p.o. In this assay as well as in sum total of all other assays, indicative of neuroleptic activity, performed on the two above-identified compounds, both compounds appear of comparable potency and efficacy as potential neuroleptics.

Surprisingly and unexpectedly, the compound of the subject invention either does not have or exhibits a very low propensity to extrapyramidal side effects as compared to the next lowest homolog described above. This is a surprising and unexpected result since most neuroleptics exhibit extrapyramidal side effects and certainly one would expect such side effects for the compounds of the invention, especially when structurally related prior art components (next lower homolog) appear to exhibit a propensity toward such side effects.

The propensity for extrapyramidal side effects can be determined by apomorphine sterotypy and apomorphine emesis tests. The tests are carried out in the manner described below.

Groups of male Wistar rats (125–200 gms) are used and food and water are available ad libitum. Drugs are prepared using distilled water and, if insoluble, a suitable surfactant is added. The route of administration may be varied and the dosage volume is 10 ml/kg.

For a primary screen a group size of six is used. The drug is administered one hour prior to apomorphine challenge and the animals are caged. The control group receives vehicle. Apomorphine HCl is prepared at a concentration of 12.5 mg/10 ml in 1% saline. Apormorphine HCl is administered at a dose of 1.25 mg/kg, intravenously, with a dosage volume of 1 ml/kg. At 5, 10 and b 20 minutes after apomorphine administration animals are briefly observed and agitation and sterotypic behavior are noted. Agitation is defined as restless motion and its presence (1) or absence (0) is scored. Stereotypic activity is defined as sniffing, licking, or chewing behavior which occurs in a repetitive manner and is rated as follows:

0: no unusual activity
1: occasional sniffing, licking, or chewing but with periods of normal behavior longer than periods of stereotypic behavior,
2: frequent sniffing, licking, or chewing but with occasional periods of normal behavior shorter than periods of stereotypic behavior,
3: constant sniffing, licking, or chewing without interruption.

The scores for the two parameters (agitation and stereotypy) are separately added and averaged for each animal. Any animal with an averaged response of less than the control scores in either parameter is considered to show anti-apomorphine activity for that parameter. The percent effectiveness of a drug is determined to be the percent inhibition shown by the drug.

A dose response is run in the same manner as a primary screen except that a group size of ten is used and the animals are dosed in a randomized manner. One group receives vehicle. $ED_{50}$'s for agitation and/or stereotypy are calculated by means of probit analysis.

Inhibition of apomorphine induced emesis in the dog is as follows. Adult beagle dogs of either sex are used in treatment groups of 3 to 9 dogs per dose. The dogs are housed in individual cages where water is available ad libitum and feed is presented once a day. The dogs are given the test compound orally as a mixture with lactose in a gelatin capsule. They are then dosed with a standard 0.15 mg/kg dose of apomorphine hydrochloride subcutaneously at various intervals after administration of the test compound. The initial screen is usually a dose of 1 mg/kg orally of the test compound. The dogs are first observed for overt behavioral effects, e.g., pupillary response to light, changes in salivation, sedation, tremors, etc. After the administration of apomorphine, the dogs are observed for stereotype sniffing and gnawing, and the emetic response. Emesis is defined as wretching movements followed by an opening of mouth and either attempted or successful injection of stomach content.

If the experimental compound is anti-emetic in the primary screen, the dose is progressively lowered to obtain a minimal effective dose (MED) and/or an $ED_{50}$ value.

A computerized probit-analysis is used to calculate the data for $ED_{50}$ values and 95% confidence limits.

Activity in both apomorphine stereotypy and apomorphine emesis tests is indicative of dopamine blocking activity in the striatum, an area of the brain which is believed to be involved in extrapyramidal side effects in neuroleptics. For example, clozapine, a well-known neuroleptic, exhibits a negative activity in apomorphine stereotypy inhibition in rats (agitation: negative at 50 mg/kg; stereotypy: negative at 50 mg/kg) and is inactive from 2 to 10 mg/kg (orally) in apomorphine induced emesis in the dog. Clinically, clopazine has been shown to have a low incidence of extra-pyramidal activity.

It has been found that 3-{3-[4-(4-fluorobenzoyl)-piperidyl]propyl} indole, revealed in U.S. Pat. No. 4,046,900, is quite active in both tests. In apomorphine induced stereotypy it demonstrates a 50% blocking action of the agitation phase at 2.5 mg/kg (Intraperitoneally) and of the stereotypy phase at 3.7 mg/kg (intraperitoneally). In apomorphine emesis, it produces 100% blockage at both 1 and 5 mg/kg orally of the emesis produced by a 0.15 mg/kg dose of apomorphine hydrochloride. On the other hand, the compound of the invention 3-{3-[4-(4-fluorobenzoyl)piperidyl]propyl}-2-methyl indole, is inactive in the apomorphine stereotypy assay at a dose of 25 mg/kg (subcutaneously) and shows only marginal activity of 33% inhibition in the apomorphine emesis test at a dose of 5 mg/kg orally. Thus, the prior art compound 3-}3-[4-(4-fluorobenzoyl)-piperidyl]propyl} indole displays the likelihood of extrapyramidal side effects while the compound of the invention 3-{3-[4-(4-fluorobenzoyl)piperidyl]propyl}-2-methyl indole tested at similar or higher doses does not.

The compounds of the present invention may be administered to a patient by a convenient route such as orally, intramuscularly, intravenously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 7% to about 70% by weight of the unit. The amount of active compound in such compositions is such that a suitable dosage will be obtained. Preferred compositions and preparations according to the present invention are prepared so that an oral dosage unit form contains between 1 and 200 milligrams of active compound.

The tablets, pills, capsules, troches and the like may also contain the following ingredients: a binder such as gum tragacanth or gelatin; an excipient such as starch or lactose, a disintegrating agent such as alginic acid, potato starch and the like; a lubricant such as magnesium stearate; and a sweetening agent such as sucrose or saccharin may be added or a flavoring agent such as peppermint, methyl salicylate, or orange flavoring.

When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or both. A syrup may contain, in addition to the active compounds sucrose as a sweetening agent, and certain preservatives, dyes and colorings, and flavors. Materials used in preparing these various compositions must be pharmaceutically pure and non-toxic in the amounts utilized.

For the purpose of parenteral therapeutics administration, the active compounds of the invention may be incorporated into a solution of suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The invention is further illustrated by the following example given for illustrative purposes. In view of the amendments to the Manual of Patent Examining Procedure, including Sections 6φ8.φ1 (p); 7φ7.φ7(1); 2φφ4; 2φ21 dated Jan., 1981 and received on or about the week of Sept. 14, 1981, the EXAMPLE of the specification is to be read as if it was expressed in the past tense since it is an example which has actually been carried out.

EXAMPLE

3-{3-[4-(4-Fluorobenzoyl)piperidyl]propyl}-2-methylindole

A mixture of 3-(3-bromopropyl)-2-methylindole (13.8 g), 4-(4-fluorobenzoyl)piperidine (6.0 g), $K_2CO_3$ (4.0 g) and dimethylformamide (DMF) (100 ml) is stirred and heated at 50° C. under $N_2$ for 16 hours. The mixture is poured into $H_2O$, and the aqueous mixture extracted with benzene, the benzene extract is washed with $H_2O$, dried ($Na_2SO_4$), and the solvent evaporated to leave an oil. The oil is taken up in ether and HCl (g) is bubbled into it to precipitate 10.6 g of a hydrochloride salt. The salt is converted to the free base (an oil). Upon trituration of the oil with ether 4.2 g of a solid is collected. The solid is recrystallized from EtOH-$H_2O$ (charcoal treatment), and then twice from isopropanol to yield 1.9 g (15%), m.p. 135°–137° of 3-{3-[4-(4-fluorobenzoyl)-piperidyl]propyl} 2-methylindole.

ANALYSIS: Calculated for $C_{24}H_{27}FN_2O$: 76.16%C; 7.19%H; 7.40%N; 5.02%F. Found: 75.76%C; 7.14%H; 7.56%N; 5.30%F.

We claim:

1. A compound of the formula

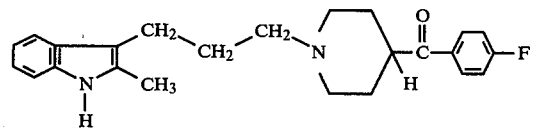

or an acid addition salt thereof prepared from a pharmaceutically acceptable acid.

2. A method of depressing the central nervous system which comprises administering to a patient a pharmaceutically effective amount of 3-{3-[4-(4-fluorobenzoyl)piperidyl]-propyl} -2-methyl indole or an acid addition salt thereof prepared from a pharmaceutically acceptable acid.

3. A neuroleptic composition which comprises as an active ingredient the compound 3-{3-[4(4-fluorobenzoyl)piperidyl]-propyl}-2-methyl indole or an acid addition salt thereof prepared from a pharmaceutically acceptable acid in an amount sufficient to depress the central nervous system, and an inert carrier.

4. The composition as defined in claim 3 wherein said active ingredient is present in an amount of between 0.5 and about 70% by weight.

* * * * *